(12) United States Patent
Johnson

(10) Patent No.: US 7,927,630 B2
(45) Date of Patent: Apr. 19, 2011

(54) USE OF AUTOLOGOUS SEDIMENT FROM FLUID ASPIRATES AS VEHICLES FOR DRUG DELIVERY

(76) Inventor: Lanny L. Johnson, Okemos, MI (US)

(*) Notice: Subject to any disclaimer, the term of this patent is extended or adjusted under 35 U.S.C. 154(b) by 427 days.

(21) Appl. No.: 11/518,800

(22) Filed: Sep. 11, 2006

(65) Prior Publication Data

US 2007/0059372 A1    Mar. 15, 2007

Related U.S. Application Data

(60) Provisional application No. 60/716,064, filed on Sep. 12, 2005.

(51) Int. Cl.
*A61K 35/24* (2006.01)
*A61K 35/37* (2006.01)
*A61B 5/00* (2006.01)
*B65D 81/00* (2006.01)

(52) U.S. Cl. ......... 424/537; 600/576; 600/578; 600/583

(58) Field of Classification Search .................. 600/576, 600/578, 583
See application file for complete search history.

(56) References Cited

U.S. PATENT DOCUMENTS

| | | | |
|---|---|---|---|
| 5,004,681 A | 4/1991 | Boyse et al. |
| 5,192,553 A | 3/1993 | Boyse et al. |
| 5,197,985 A | 3/1993 | Caplan et al. |
| 5,226,914 A | 7/1993 | Caplan et al. |
| 5,811,094 A | 9/1998 | Caplan et al. |
| 5,842,477 A | 12/1998 | Naughton et al. |
| 5,908,784 A | 6/1999 | Johnstone et al. |
| 6,080,194 A | 6/2000 | Pachence et al. |
| 6,174,333 B1 | 1/2001 | Kadiyala et al. |
| 6,387,369 B1 | 5/2002 | Pittenger et al. |
| 6,461,645 B1 | 10/2002 | Boyse et al. |
| 6,569,427 B1 | 5/2003 | Boyse et al. |
| 6,602,294 B1 | 8/2003 | Sittinger et al. |
| 6,605,275 B1 | 8/2003 | Boyse et al. |
| 6,815,416 B2 * | 11/2004 | Carney et al. ............. 514/2 |
| 7,442,389 B2 * | 10/2008 | Quelle et al. ............ 424/489 |
| 2002/0122790 A1 | 9/2002 | Hunziker |
| 2003/0130250 A1 | 7/2003 | Bridger et al. |
| 2004/0028717 A1 | 2/2004 | Sittinger et al. |

OTHER PUBLICATIONS

Centrifugation Handout, www.tulane.edu/~wiser/methods/handouts/class/06_centrif.pdf, accessed Sep. 29, 2009, pp. 1-5.*
Chen, Mesenchymal stem cells in arthritic diseases, Arthritis Res Ther., 2008;10(5):223 (abstract only).

(Continued)

*Primary Examiner* — Sandra Saucier
(74) *Attorney, Agent, or Firm* — Biotech Beach Law Group PC; Raymond Wagenknecht

(57) ABSTRACT

A method of using fluid aspirates as vehicles for drug delivery by collecting a fluid aspirate such as synovial joint effusion, pleural effusion, pericardial effusion, or ascites from a patient and centrifuging the fluid aspirate to provide a supernatant and a sedimented material. The sedimented material can optionally be further purified. One or more factors such as cytokines, bone morphogenetic proteins (BMPs), pharmaceutical drugs and gene vectors are added to the sedimented material or supernatant, optionally also including a biologically compatible medium such as a bioabsorbable sponge, so as to provide a vehicle for the one or more factors for reintroducion into the patient.

18 Claims, 1 Drawing Sheet

OTHER PUBLICATIONS

Crawford, Synovial Fluid Stem Cells, European Cells and Materials, vol. 16 Suppl. 2, 2008, p. 41 (abstract only).

De Bari, Multipotent mesenchymal stem cells from adult human synovial membrane, Arthritis Rheum. 2001; 44(8):1928-42 (abstract only).

Jones, Enumeration and phenotypic characterization of synovial fluid . . . , Arthritis Rheum. 2004; 50(3):817-27 (abstract only).

Jones, Synovial fluid mesenchymal stem cells in health and early osteoarthritis, Arthritis Rheum. Jun. 2008; 58(6):1731-40 (abstract only).

McGonagle, A potential role for synovial fluid mesenchymal stem cells in ligament regeneration, Rheumatology 2008; 47(8):1114-1116.

Morito, Synovial fluid-derived mesenchymal stem cells . . . , Rheumatology 2008; 47(8):1137-1143 (abstract only).

Pei, Engineering of functional cartilage tissue using stem cells from synovial lining: a preliminary study, Clin Orthop Relat Res. 2008; 466(8):1880-9.

De Bari et al., Arthritis & Rheumatism, vol. 50, n. 1, pp. 142-150, 2004.

* cited by examiner

USE OF AUTOLOGOUS SEDIMENT FROM FLUID ASPIRATES AS VEHICLES FOR DRUG DELIVERY

PRIORITY

The present application claims priority under 35 USC section 119 and provisional application Ser. No. 60/716, 064 filed on Sep. 12, 2005.

STATEMENT REGARDING FEDERALLY SPONSORED RESEARCH OR DEVELOPMENT

Not Applicable

BACKGROUND OF THE INVENTION (1) Field of the Invention

The present invention relates generally to vehicles for delivering one or more factors such as cytokines, bone morphogenetic proteins (BMPs), pharmaceutical drugs and gene vectors. Specifically, the present invention relates to the use of autologous sediment from fluid aspirates as delivery vehicles.

(2) Description of the Related Art

Solutions, suspensions and emulsions have been used throughout the years as vehicles for delivery of the active ingredients of pharmaceutical drugs. These delivery vehicles do not allow for the maintenance of effective dosage levels of the active ingredients in the bloodstream. Sustaining a dosage of a therapeutic factor may require multiple injections, which can increase the likelihood of infection. Therapeutic factors such as pharmaceutical drugs and recombinant proteins often require controlled and sustained release at specific target tissues to be safe and effective. If there is a narrow difference between therapeutic and toxic levels (therapeutic index) of a drug it will require strict compliance to an injection schedule by the patient. Additionally, cytokines such as IL-2 have a danger of systemic toxicity. IL-2 has useful local therapeutic potential, but systemically it can cause vascular shock and pulmonary edema. Another concern is that therapeutic peptides have a very short half-life, so that targeted, controlled and sustained release is important for their effectiveness.

Recent advancements in the field of delivery vehicles allow for the controlled and sustained delivery of drugs. The advancements include such technologies as osmotic pumps, liposomes, dendrimers, and microencapsulation in biodegradable polymers such as microparticles, microspheres or nanoparticles. U.S. Pat. No. 4,489,055 to Couvreur et al., for example, describes biodegradable particles of alkyl-cyanoacrylate containing a biologically active substance. Particles comprised of various polymers and copolymers, such as PLG [poly(lactide-co-glycolide)], PCL [poly( ,-caprolactone)], PLA [poly(L-lactic acid)] and PBLA [poly($\exists$-benzyl-L-aspartate)] have been described (M. Ravi Kumar *J. Pharm. Parmaceut. Sci.* 3(2): 234-258, 2000). Alginate (including calcium alginate beads encapsulated with poly-L-lysine) and chitosan have both been used extensively to create microcapsules and microspheres. Maintaining a minimal inflammatory response to the vehicle is important in any design for a delivery vehicle that is to be placed within the human body. Other advancements which allow for targeted and controlled release of factors include gene therapy. The use of a patient's own cells to carry the factor avoids some of the issues relating to immune rejection, since the drug vehicle is autologous.

One difficult tissue of the body to target with drugs or other factors is the synovium. Some have described the use of synovial fluid constituents for injection. For example, U.S. Pat. No. 4,141,973 to Balazs describe a purified high molecular weight hyaluronic acid fraction extracted from animal tissues for injection into a joint. U.S. Pat. No. 5,079,236 to Drizen et al. describe a purified high molecular weight hyaluronic acid fraction for treatment of joint disease in animals. HYALGAN® sodium hyaluronate (Sanofi-Synthelabo Inc, New York, N.Y.) is a purified hyaluronate from rooster combs for injection into knee joints for the purpose of pain relief. U.S. Pat. No. 6,699,471 B2 and U.S. Patent Application Publication No. 2004/0142465 A1 to Radice et al. describe injectable compositions having hyaluronic acid derivatives and cells such as chondrocytes for the treatment of soft tissues. CARTICEL® autologous cultured chondrocytes (Genzyme, Cambridge, Mass.) are presently used for the repair of articular cartilage defects caused by acute or repetitive trauma. The therapeutic chondrocytes are derived from an in vitro expansion of autologous chondrocytes harvested from the normal, femoral articular cartilage of the patient to be treated. The cells are isolated and expanded, then implanted into the articular cartilage defect beneath an autologous periosteal flap sutured over the cartilage defect.

The synovium and synovial fluid in patients with rheumatoid arthritis are known to have upregulated proinflammatory cytokines. Antiinflammatory agents are activated in the disease, but do not counter the proinflammatory response. Interferon-$\exists$ (IFN-$\exists$) is a natural anti-inflammatory, because it downregulates proinflammatory cytokines such as IL-1$\exists$ and tumor necrosis factor-$\forall$ (TNF-$\forall$) while also increasing the IL-1 receptor antagonist in synoviocytes. Van Holten et al. (*Arth. Res.*, vol. 6, no. 3) teach treatment in an animal model of rheumatoid arthritis using intraperitoneal injections of IFN-$\exists$ to ameliorate the arthritis. However, this requires systemic treatment with the IFN-$\exists$. Locally targeted therapy would be desirable. Bandara et al., *Proc. Natl. Acad. Sci, USA*, vol. 90, pp. 107641-10768 (1993) and Makarov et al., *Proc. Natl. Acad. Sci, USA*, vol. 93, pp. 402-406 (1996) take another approach by transducing synoviocytes with a cDNA so as to express the interleukin 1 receptor-antagonist (IL-1ra) protein. Del Vecchio et al. (*Arth. Res.*, vol. 3, no. 4) teach approaches to enhance the transduction of human synoviocytes with the interleukin 1 receptor-antagonist (IL-1ra) cDNA. The ex vivo transfer of genes for delivering genes to the synovial lining of joints seems to selectively target type B synoviocytes. In vivo gene delivery by intra-articular injection of adenovirus vectors apparently transduces leukocytes and both type A and B synoviocytes (Evans, *Arth. Res.*, vol. 1 no. 1, pp. 21-24, 1999). Research by Ghivizzani et al. (*Proc Natl Acad Sci, USA* 1998, 95:4613-4618) shows a contralateral effect of in vivo gene delivery, which suggests that transduced leukocytes have the capacity to traffic between joints.

While the related art teach various drug delivery vehicles which give controlled and sustained release, and while some related art utilize synovial fluid constituents such as hyaluronic acid for the treatment of joint disease, there still exists a need for improved delivery vehicles for factors, such as drugs, gene vectors and cytokines which allow for targeted, controlled and sustained release of the factors.

OBJECTS

Therefore, it is an object of the present invention to provide a means to deliver one or more factors to a patient.

It is further an object of the present invention to provide a means to deliver of one or more factors to the patient utilizing autologous material so as to minimize any inflammatory response.

These and other objects will become increasingly apparent by reference to the following description.

SUMMARY OF THE INVENTION

The present invention provides a method of delivering one or more factors to a patient which comprises collecting a fluid aspirate from the patient, centrifuging the fluid aspirate to provide a supernatant and a sedimented material, separating the supernatant from the sedimented material, immersing the sedimented material in a solution comprising one or more factors so as to provide a treated sediment, and introducing the treated sediment to deliver the one or more factors to the patient.

In further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof. In still further embodiments the sedimented material after separating, and before immersing, is examined and treated to remove unwanted components, to supply wanted components or both.

The present invention provides a method of delivering one or more factors to a patient which comprises collecting a fluid aspirate from the patient, centrifuging the fluid aspirate to provide a supernatant and a sedimented material, separating the supernatant from the sedimented material, immersing the sedimented material in a solution comprising one or more factors, pressurizing the sedimented material in the solution comprising one or more factors so as to provide a treated sediment, and introducing the treated sediment to deliver the one or more factors to the patient.

In further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof. In still further embodiments the sedimented material after separating, and before immersing, is examined and treated to remove unwanted components, to supply wanted components or both.

The present invention provides a method of delivering one or more factors to a patient which comprises collecting a fluid aspirate from the patient, centrifuging the collected fluid aspirate to provide a supernatant and sedimented material, separating the supernatant from the sedimented material, immersing the sedimented material in a solution comprising one or more factors to provide a treated sediment, placing the treated sediment into a biologically compatible medium, and introducing the treated sediment and biologically compatible medium into a tissue of the patient so as to deliver the one or more factors to the patient.

In further embodiments the biologically compatible medium is blood or a fibrin blood clot. In still further embodiments the biologically compatible medium is a bioabsorbable sponge. In still further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof. In still further embodiments the sedimented material after separating, and before immersing, is examined and treated to remove unwanted components, to supply wanted components or both.

The present invention provides a method of delivering one or more factors to a patient which comprises collecting a fluid aspirate from the patient, centrifuging the collected fluid aspirate to provide a supernatant and sedimented material, separating the supernatant from the sedimented material, immersing the sedimented material in a solution comprising one or more factors, pressurizing the sedimented material in the solution comprising one or more factors so as to provide a treated sediment, placing the treated sediment into a biologically compatible medium, and introducing the treated sediment and biologically compatible medium into a tissue of the patient so as to deliver the one or more factors to the patient.

In further embodiments the biologically compatible medium is blood or a fibrin blood clot. In still further embodiments the biologically compatible medium is a bioabsorbable sponge. In still further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof. In still further embodiments the sedimented material after separating, and before immersing, is examined and treated to remove unwanted components, to supply wanted components or both.

The present invention provides a method of delivering one or more factors to a patient which comprises collecting a fluid aspirate from the patient, centrifuging the fluid aspirate to provide a supernatant and a sedimented material, separating the supernatant from the sedimented material, purifying a one or more components of the sedimented material, immersing the one or more components in a solution comprising one or more factors so as to provide a treated vehicle, and introducing the treated vehicle to deliver the one or more factors to the patient.

In further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof. In still further embodiments the purified components of the purification step are examined to determine the purity of the components prior to immersing.

The present invention provides a method of delivering one or more factors to a patient which comprises collecting a fluid aspirate from the patient, centrifuging the fluid aspirate to provide a supernatant and a sedimented material, separating the supernatant from the sedimented material, purifying a one or more components of the sedimented material, immersing the one or more components in a solution comprising one or more factors, pressurizing the one or more components in the solution comprising one or more factors so as to provide a treated vehicle, and introducing the treated vehicle to deliver the one or more factors to the patient.

In further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof. In still further embodiments the treated vehicle is examined in the step of pressurizing, before being introduced into the patient.

The present invention provides a method of delivering one or more factors to a patient which comprises collecting a fluid aspirate from the patient, centrifuging the collected fluid aspirate to provide a supernatant and sedimented material, separating the supernatant from the sedimented material, purifying a one or more components of the sedimented material, immersing the one or more components in a solution comprising one or more factors, placing the one or more components in the solution comprising one or more factors into a biologically compatible medium so as to provide a treated vehicle, and introducing the treated vehicle into a tissue of the patient so as to deliver the one or more factors to the patient.

In further embodiments the biologically compatible medium is blood or a fibrin blood clot. In still further embodiments the biologically compatible medium is a bioabsorbable sponge. In still further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof. In still further embodiments the purified components of the purifying step are examined to determine the purity of the components prior to the immersing step.

The present invention provides a method of delivering one or more factors to a patient which comprises collecting a fluid aspirate from the patient, centrifuging the collected fluid aspirate to provide a supernatant and sedimented material, separating the supernatant from the sedimented material, purifying a one or more components of the sedimented material, immersing the one or more components in a solution comprising one or more factors, pressurizing the one or more components in the solution comprising one or more factors, placing the one or more components in the solution comprising one or more factors into a biologically compatible medium so as to provide a treated vehicle, and introducing the treated vehicle into a tissue of the patient so as to deliver the one or more factors to the patient. In still further embodiments the purified components of the purifying step are examined to determine the purity of the components prior to the immersing step.

In further embodiments the biologically compatible medium is blood or a fibrin blood clot. In still further embodiments the biologically compatible medium is a bioabsorbable sponge. In still further embodiments the fluid aspirate is synovial joint effusion, pleural effusion, pericardial effusion, or ascites. In still further embodiments the one or more factors are introduced to repair cartilage in a joint. In still further embodiments the one or more factors are cytokines, bone morphogenetic proteins (BMPs), pharmaceutical drugs, gene vectors or mixtures thereof.

The present invention provides a method of delivering one or more factors to a patient which comprises: (a) collecting a fluid aspirate from the patient; (b) centrifuging the fluid aspirate to provide a supernatant and a sedimented material; and (c) separating the supernatant from the sedimented material; (d) providing one or more factors to the supernatant so as to provide a mixture; and (e) injecting the mixture into the patient to deliver the one or more factors to the patient. In further embodiments the fluid aspirate is synovial joint effusion, pleural effusion, pericardial effusion, or ascites. In still further embodiments the one or more factors are injected to repair cartilage in a joint. In still further embodiments the one or more factors are a cytokine. In still further embodiments the one or more factors are bone morphogenetic proteins (BMPs). In still further embodiments the one or more factors are a pharmaceutical drug. In still further embodiments the one or more factors are a gene vector.

The present invention provides a method of delivering one or more factors to a patient which comprises: (a) collecting a fluid aspirate from the patient; (b) centrifuging the collected fluid aspirate to provide a supernatant and sedimented material; and (c) separating the supernatant from the sedimented material; (d) placing a biologically compatible medium into the supernatant; (e) providing one or more factors to the supernatant and biologically compatible medium so as to provide a therapeutic mixture; and (f) placing the therapeutic mixture into a tissue of the patient so as to deliver the one or more factors to the patient.

In further embodiments the biologically compatible medium is blood or a fibrin blood clot. In still further embodiments the biologically compatible medium is a bioabsorbable sponge. In still further embodiments the fluid aspirate is synovial joint effusion, pleural effusion, pericardial effusion, or ascites. In still further embodiments the one or more factors are to repair cartilage in a joint. In still further embodiments the one or more factors are cytokines, bone morphogenetic proteins (BMPs), pharmaceutical drugs, or gene vectors. In still further embodiments the supernatant after step (c) is examined and treated to remove unwanted components.

DETAILED DESCRIPTION OF THE INVENTION

Figure 1:
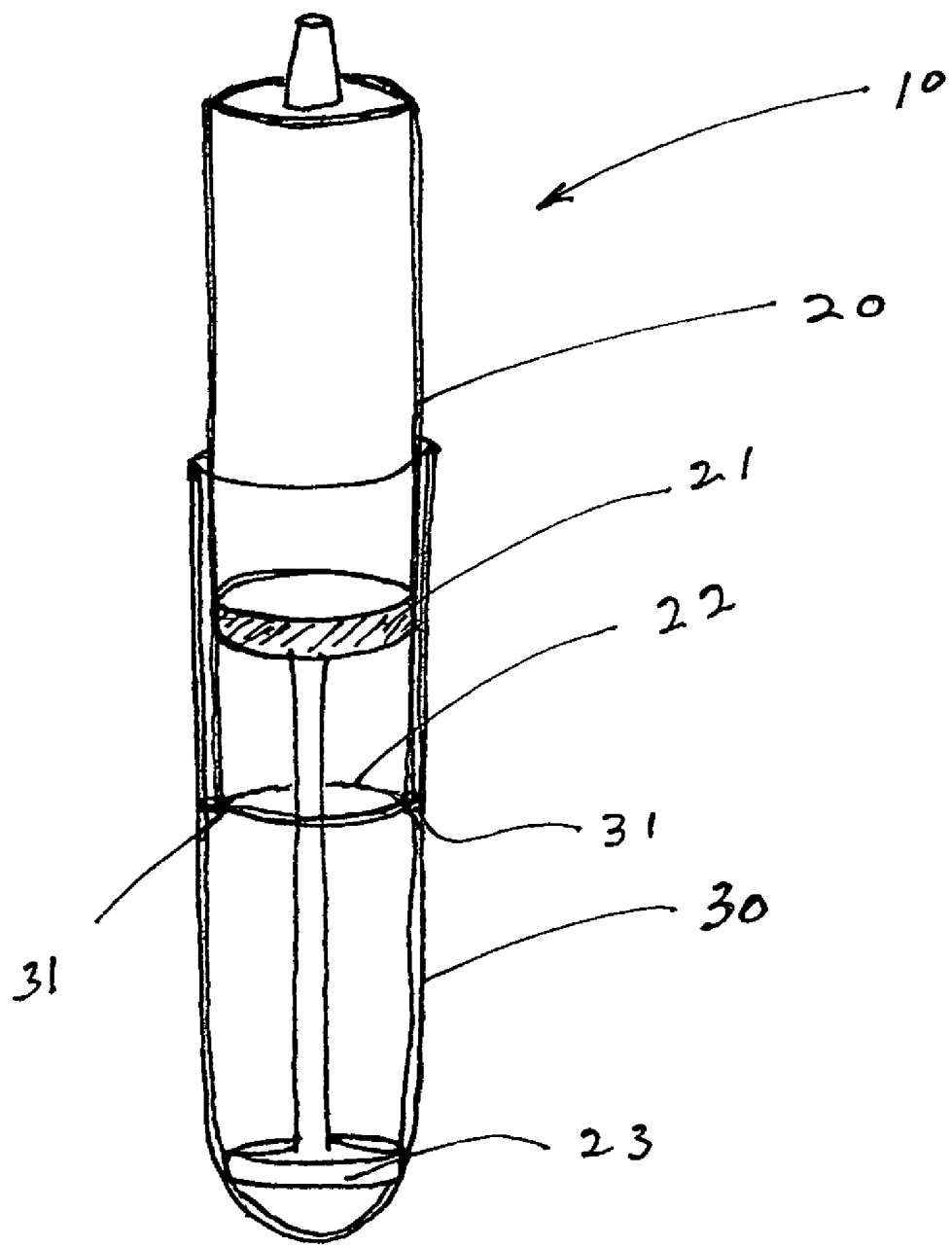
FIG. 1 is a side view of a centrifuge tube (10) having a collection tube (20) that doubles as pressure chamber and a delivery syringe and home for the drug or drug combination which can be used to perform the method of the present invention.

All patents, patent applications, government publications, government regulations, and literature references cited in this specification are hereby incorporated herein by reference in their entirety. In case of conflict, the present description, including definitions, will control.

Synovium constitutes the lining of synovial joints. It consists of series of cells covering lining of fat and vascularity. The cells secrete synovial fluid. These cells naturally shed and can be found in small numbers in synovial fluid. In joint inflammation the lining proliferates into fingerlike projections called villi. These finger like projections are lined with synovial cells and filled with fat and vessels. Therefore there are synovial cells, fat cells with potential for some stem cells, fibroblasts, blood with monocytes and lymphocytes plus angioblasts. The latter are there related to the reaction of the synovium and the increased vascularity. It has been reported by Hunziker and Rosenberg that synovium will grow over cartilage and heal a laceration in cartilage (J Bone Joint Surg Am. 1996 May; 78(5):721-33).

Body fluids such as synovial fluid contain a variety of materials that when isolated can serve as vehicles for drug and gene delivery. For example the synovial joint effusion that accompanies degenerative arthritis has a variety of debris. The fluid can be removed by arthrocentesis. The fluid contains cellular and tissue debris that is often visible to the naked eye. When subjected to centrifuging, the material is separated out and collectable from the centrifuge tube. (Johnson, L L. Arthroscopic Surgery Principles and Practice. C. V. Mosby 1986, St. Louis). When joint fluid undergoes centrifugation the sediment has components including, but not limited to white blood cells, red blood cells, synovial cells, synovial fragments, and articular cartilage fragments with and without viable appearing cells.

Protocol: One embodiment of the method involves the separation of the autologous joint fluid tissue debris by centrifuging and discarding the supernatant. The sediment from the centrifugation is saved. Optionally, blood or a fibrin blood clot can be added. The sediment is immersed in one or more factors, for example a drug or gene vector, for up to 30 minutes. The one or more factors is adsorbed over various times onto the various components which make up the sediment. Actuation of pressure on the debris and the factors is one means encompassed by the present invention to increase the saturation of the drug or other factors in the debris. The autologous sediment with adsorbed drug or gene vector is then injected into the patient for the intended purpose. The drug or gene vector is selectively released from each constituent of the sediment at a different rate, according to cell and tissue type, giving a prolonged and even timed release of the drug. In one embodiment shown in FIG. 1, a sterile, disposable centrifuge tube (10) is used for performing the methods of the present invention which can be used during outpatient surgery, or in a hospital surgery operating theater. The centrifuge tube (10) apparatus has a collection tube (20) that doubles as pressure chamber and a delivery syringe and home for the drug or drug combination. In one example, the centrifuge tube (10) apparatus comprises a collection tube (20) that doubles as a delivery syringe which is inverted within a holder (30) during centrifugation. The collection tube (20) rests upon ledges (31) in the holder (30) so that a plunger (21) remains towards an open end (22) of the collection tube (20) during centrifugation. The collection tube (10) can be removed from the holder (30) after separation of the sediment from the fluid. The supernatant can then be removed from the collection tube (20) by pressing the handle (23). The remaining sediment can then be resuspended by shaking or vortexing. Another example of a centrifugation syringe which can be utilized to perform the method of the present invention is disclosed in U.S. Pat. No. 5,577,513 to Van Vlasselaer hereby incorporated herein by reference in its entirety. The delivery instrument could be as simple as a syringe and needle. The material could be delivered in a autogenous fibrin blood clot, via a bioabsorbable sponge, or injected under a patch of autogenous tissue.

One example of this is the treatment of cartilage injury or disease. The injured or degenerative joint has fluid with cells, cell debris, synovium, synovial cells, cartilage matrix, cartilage with matrix and cells. A cytokine such as one of the Bone Morphogenetic Proteins (BMPs) is mixed with sediment. The combination is then placed into the joint with or without a medium such as a bioabsorbable sponge. BMPs are proteins within the transforming growth factor- beta (TGF-$\beta$) superfamily which bind to serine/threonine transmembrane receptors that phosphorylate Smad second messenger family proteins which regulate transcription of various genes. A subfamily of BMPs, called GDFs, are localized in joints during development and therefore may be critical for synovial joint morphogenesis. The BMPs, among other growth factors, can be delivered directly as a protein or via gene vectors. Other examples of sediments from fluid aspirates which can be used to provide vehicles for delivery of factors such as drugs and genes are those obtained from pleural effusion, pericardial effusion and ascites.

In another embodiment, the supernatant fluid remaining after centrifugation is utilized. In this embodiment, the particles would be removed and only the lubricant proteins would remain in the synovial fluid. Cartilage debris is thereby removed. The proteins which are in the supernatant are analyzed, and then mixed with one or more factors, for example BMP, and reinjected into the patient. A disposable centrifuge tube (10) such as described previously is used. The syringe can be already coated with one or more factors, such as BMP, when aspirating the surface synovial fluid in the centrifuge tube (10). The contents of the syringe are then injected at a certain time interval. In some embodiments the contents are injected immediately.

Optionally, in some embodiments, the precipitated tissues are examined for diagnostic purposes prior to use. Some materials which have been collected may be detrimental to the patient and these unwanted components must be removed, while other materials may be helpful to reintroduce into a patient. For example, certain proteins and or cellular debris may cause an immune response or inflammation in the patient. In some embodiments which utilize the supernatant for introduction into the patient, specific proteins or all proteinaceous material can be extracted or bound before the patient receives the supernatant materials. For diagnostic analysis, the materials can be centrifuged and the precipitates and smears of the supernatant can be examined morphologically and histochemically for their nature and acceptability for purity and subsequent use. The precipitant can be examined including placement in paraffin blocks for histological analysis.

EXAMPLE

A synovial joint fluid aspirate is to be collected from a knee joint of a patient. The fluid aspirate is then centrifuged to provide a supernatant and a sedimented material. The supernatant is then be removed from the sedimented material and one or more factors such as cytokines and bone morphogenetic proteins (BMPs) are then provided to the supernatant so as to provide a therapeutic mixture. Prior to injecting the mixture into the patient to deliver these factors, the mixture can be tested on alternate knees in a laboratory animal to determine whether the prepared therapeutic mixture is sufficiently clean. Treated versus untreated knees of the laboratory animal can be then compared. If it is determined that the mixture is sufficiently clean, the therapeutic mixture can be then be injected into the knee of the patient which requires treatment.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

I claim:

1. A method of delivering one or more factors to an injured or degenerative joint of a patient which comprises:
   (a) collecting a fluid aspirate from the injured or degenerative joint of the patient, wherein the injured or degenerative joint comprises synovial villi;
   (b) centrifuging the fluid aspirate to provide a supernatant and a sedimented material, wherein the sedimented material comprises cellular components;
   (c) separating the supernatant from the sedimented material;
   (d) immersing the sedimented material in a solution comprising one or more factors to stimulate cartilage growth so as to provide a treated sediment; and
   (e) introducing the treated sediment to deliver the one or more factors to the joint of the patient, wherein the method is performed with a centrifuge tube apparatus comprising a syringe and a holder, wherein the syringe comprises a collection tube comprising an end with a narrowed outlet and a means for connection to a needle and an open end, wherein the syringe further comprises a plunger inserted into the open end, wherein steps (a), (c), (d) and (e) are performed using the syringe, and wherein during step (b) the syringe rests in an inverted position upon ledges in the holder so that the plunger remains towards the open end of the syringe.

2. The method of claim 1 wherein the sedimented material after step (c), and before step (d), is examined and treated to remove unwanted components, to supply wanted components or both.

3. The method of claim 1 wherein the fluid aspirate is synovial joint effusion, pleural effusion, pericardial effusion, or ascites.

4. The method of claim 1 wherein the one or more factors are introduced to repair cartilage in a joint.

5. The method of claim 1 wherein the step of immersing the sedimented material in the solution further comprises pressurizing the sedimented material in the solution.

6. The method of claim 1 further comprising a step of placing the treated sediment into a biologically compatible medium, further wherein the introduced treated sediment is introduced together with the biologically compatible medium.

7. The method of claim 6 wherein the biologically compatible medium is blood or a fibrin blood clot.

8. The method of claim 6 wherein the biologically compatible medium is a bioabsorbable sponge.

9. The method of claim 1 further comprising a step of purifying one or more sediment components from the sedimented material to form a purified sedimented material, further wherein the step of immersing sedimented material is immersing purified sedimented material.

10. The method of claim 9 wherein the purity of the one or more sediment components is determined further comprising determining the purity of the one or more sedimented components.

11. The method of claim 9 further comprising a step of placing the treated sediment into a biologically compatible medium, wherein the introduced treated sediment is introduced together with the biologically compatible medium.

12. The method of claim 1 wherein the cellular components are synovial cells or synovial fragments.

13. The method of claim 1 wherein the cellular components are articular cartilage fragments.

14. The method of claim 1 wherein the cellular components are fibroblasts or angioblasts.

15. The method of claim 1 wherein the cellular components comprise stem cells.

16. The method of claim 1 wherein the one or more factors to stimulate cartilage growth are selected from the group consisting of a cytokine, a bone morphogenetic protein (BMP) and a BMP encoding nucleic acid molecule in a nucleic acid vector.

17. The method of claim 1 wherein the treated sediment is introduced to intra-articular structures selected from the group consisting of a meniscus, articular cartilage, a ligament.

18. The method of claim 17 wherein the sediment is introduced during reconconstruction or grafting.

* * * * *